US00PP23057P2

(12) United States Plant Patent
Murakami

(10) Patent No.: US PP23,057 P2
(45) Date of Patent: Sep. 18, 2012

(54) ***ANGELONIA* PLANT NAMED 'SUNGELOBU'**

(50) Latin Name: *Angelonia augustifolia*
Varietal Denomination: Sungelobu

(75) Inventor: Yasuyuki Murakami, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 56 days.

(21) Appl. No.: 12/930,050

(22) Filed: Dec. 24, 2010

(51) Int. Cl.
*A01H 5/00* (2006.01)

(52) U.S. Cl. ..... Plt./404

(58) Field of Classification Search ..... Plt./404
See application file for complete search history.

*Primary Examiner* — June Hwu
(74) *Attorney, Agent, or Firm* — C. A. Whealy

(57) ABSTRACT

A new and distinct cultivar of *Angelonia* plant named 'Sungelobu', characterized by its compact and upright plant habit; freely branching habit; freely flowering habit; long flowering period; large purple violet-colored flowers; and good garden performance.

1 Drawing Sheet

Botanical designation: *Angelonia augustifolia.*
Cultivar denomination: 'SUNGELOBU'.

BACKGROUND OF THE INVENTION

The present invention relates to a new and distinct cultivar of *Angelonia* plant, botanically known as *Angelonia angustifolia*, and hereinafter referred to by the name 'Sungelobu'.

The new *Angelonia* plant is a product of a planned breeding program conducted by the Inventor in Higashiomi, Shiga, Japan. The objective of the breeding program is to create new compact, upright and freely branching *Angelonia* plants with attractive flower coloration.

The new *Angelonia* plant originated from a cross-pollination made by the Inventor in August, 2006 in Higashiomi, Shiga, Japan of a proprietary selection of *Angelonia angustifolia* identified as code number AA-04, not patented, as the female, or seed, parent with a proprietary selection of *Angelonia angustifolia* identified as code number A120-3, not patented, as the male, or pollen, parent. The new *Angelonia* plant was discovered and selected by the Inventor as a single flowering plant within the progeny of the stated cross-pollination in a controlled greenhouse environment in Higashiomi, Shiga, Japan in August, 2007.

Asexual reproduction of the new *Angelonia* plant by cuttings in a controlled greenhouse environment in Higashiomi, Shiga, Japan since September, 2007, has shown that the unique features of this new *Angelonia* plant are stable and reproduced true to type in successive generations.

SUMMARY OF THE INVENTION

Plants of the new *Angelonia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sungelobu'. These characteristics in combination distinguish 'Sungelobu' as a new and distinct *Angelonia* plant:

1. Compact and upright plant habit.
2. Freely branching habit.
3. Freely flowering habit.
4. Long flowering period.
5. Large purple violet-colored flowers.
6. Good garden performance.

Plants of the new *Angelonia* differ from plants of the female parent selection primarily in plant habit as plants of the new *Angelonia* are more compact than plants of the female parent selection. In addition, plants of the new *Angelonia* and the female parent selection differ in flower color as plants of the female parent selection have white-colored flowers.

Plants of the new *Angelonia* differ from plants of the male parent selection primarily in plant habit as plants of the new *Angelonia* are more compact than plants of the male parent selection. In addition, plants of the new *Angelonia* and the male parent selection differ in flower color as plants of the male parent selection have light pink-colored flowers.

Plants of the new *Angelonia* can be compared to plants of *Angelonia angustifolia* 'Cart Pur', disclosed in U.S. Plant Pat. No. 15,285. In side-by-side comparisons conducted in Higashiomi, Shiga, Japan, plants of the new *Angelonia* and 'Cart Pur' differed in the following characteristics:

1. Plants of the new *Angelonia* were more upright and narrower than plants of 'Cart Pur'.
2. Plants of the new *Angelonia* had larger leaves than plants of 'Cart Pur'.
3. Plants of the new *Angelonia* and 'Cart Pur' differed slightly in flower color.

BRIEF DESCRIPTION OF THE PHOTOGRAPHS

The accompanying colored photographs illustrate the overall appearance of the new *Angelonia* plant showing the colors as true as it is reasonably possible to obtain in colored reproductions of this type. Colors in the photographs may differ slightly from the color values cited in the detailed botanical description which accurately describe the colors of the new *Angelonia* plant.

The photograph at the top of the sheet comprises a side perspective view of a typical flowering plant of 'Sungelobu' grown in a container.

The photograph at the bottom of the sheet comprises a close-up view of a typical flowering plant of 'Sungelobu'.

DETAILED BOTANICAL DESCRIPTION

Plants used for the aforementioned photographs and the following observations, measurements and values were grown during the summer and autumn in 15-cm containers in a polyethylene-covered greenhouse in Higashiomi, Shiga, Japan and under typical commercial cultural practices. During the production of the plants, day temperatures averaged 22° C. and night temperatures averaged 15° C. Plants were four months old when the photographs and the description were taken. In the following description, color references are made to The Royal Horticultural Society Colour Chart, 2007 Edition, except where general terms of ordinary dictionary significance are used.

Botanical classification: *Angelonia angustifolia* 'Sungelobu'.

Parentage:

*Female, or seed, parent*.—Proprietary selection of *Angelonia angustifolia* identified as code number AA-04, not patented.

*Male, or pollen, parent*.—Proprietary selection of *Angelonia angustifolia* identified as code number A120-3, not patented.

Propagation:

*Type*.—By cuttings.

*Time to initiate roots, summer*.—About two weeks at 20° C. to 30° C.

*Time to initiate roots, winter*.—About three weeks at 20° C. to 25° C.

*Time to produce a rooted young plant, summer*.—About four weeks at 25° C. to 30° C.

*Time to produce a rooted young plant, winter*.—About five weeks at 20° C. to 25° C.

*Root description*.—Fibrous; white in color.

*Rooting habit*.—Moderate branching; medium density.

Plant description:

*Plant form/habit*.—Herbaceous perennial; compact and upright plant habit; narrow inverted triangle; freely branching habit, when pinched, about 13 lateral branches develop per plant; vigorous growth habit.

*Plant height*.—About 29.4 cm.

*Plant width (spread)*.—About 22 cm.

*Lateral branches*.—Length: About 25.2 cm. Diameter: About 2.3 mm. Internode length: About 2.8 cm. Texture: Smooth, glabrous. Color: Close to 144A.

Leaf description:

*Arrangement*.—Opposite, decussate; simple; sessile.

*Length*.—About 5.7 cm.

*Width*.—About 1 cm.

*Shape*.—Narrowly elliptic.

*Apex*.—Acute.

*Base*.—Truncate to rounded.

*Margin*.—Shallowly serrate.

*Texture, upper and lower surfaces*.—Smooth, glabrous.

*Venation pattern*.—Pinnate, reticulate.

*Color*.—Developing leaves, upper surface: Close to 143A. Developing leaves, lower surface: Close to 143B. Fully expanded leaves, upper surface: Close to 137A; venation, close to 145C. Fully expanded leaves, lower surface: Close to 137C; venation, close to 145D.

Flower description:

*Flower type/habit*.—Single bilabiate flowers arranged in terminal racemes; flowers face mostly outwardly; freely flowering habit with about 15 flowers per inflorescence; dense inflorescences.

*Fragrance*.—Faintly fragrant, pleasant.

*Natural flowering season*.—Plants begin flowering about six to seven weeks after planting; long flowering period, in the garden, flowering is continuous from late spring until autumn in Japan.

*Postproduction longevity*.—Flowers last about five days on the plant; flowers not persistent.

*Flower buds*.—Height: About 5.6 mm. Diameter: About 4.3 mm. Shape: Globose. Color: Close to 145B and N87C.

*Inflorescence height*.—About 8.1 cm.

*Inflorescence diameter*.—About 3.7 cm.

*Flower diameter*.—About 2 cm by 1.9 cm.

*Flower depth*.—About 7 mm.

*Throat diameter*.—About 6.3 mm.

*Tube length*.—About 5 mm.

*Petals*.—Quantity per flower: Bilabiate; one upper two-lobed petal and one lower three-lobed petal; petals fused at the base into a tubular throat. Length, upper lip: About 6.1 mm. Length, lower lip, lateral lobes: About 7 mm. Length, lower lip, median. lobe: About 5.5 mm. Width, upper lip: About 7.6 mm. Length, lower lip, lateral lobes: About 7.1 mm. Length, lower lip, median lobe: About 7.2 mm. Shape, upper lip: Rounded; apex, truncate to rounded. Shape, lower lip, lateral lobes: Elliptic; apex, truncate. Shape, lower lip, median lobe: Rounded; apex, rounded. Margin, upper and lower lips: Entire. Texture, upper and lower lips, upper and lower surfaces: Smooth, glabrous. Color: Upper lip, when opening and fully opened, upper surface: Close to N82B; color becoming closer to 90B with development. Lower lip, lateral lobes, when opening and fully opened, upper surface: Close to N82B; color becoming closer to 90B with development. Lower lip, median lobe, when opening and fully opened, upper surface: Close to N82B; platform, close to NN155B; nectar guides, close to 143C to 145D; color becoming closer to 90B with development. Upper and lower lips, when opening and fully opened, lower surface: Close to N82C. Throat: Close to NN155C; spots, close to N186C. Tube: Close to 86C.

*Sepals*.—Quantity per flower: Typically five in a single whorl. Length: About 2.2 mm. Width: About 1.6 mm. Shape: Ovate. Apex: Acute. Margin: Entire. Texture, upper and lower surfaces: Smooth, glabrous. Color: Immature, upper and lower surfaces: Close to 138A. Mature, upper and lower surfaces: Close to N137A.

*Pedicels*.—Length: About 0.8 mm. Diameter: About 0.4 mm. Angle: Outward. Strength: Moderately strong; flexible. Texture: Smooth, glabrous. Color: Close to N199A to N199B.

*Reproductive organs*.—Stamens: Quantity per flower: Typically four. Stamen length: About 3.6 mm. Anther shape: Oblong. Anther length: About 1.9 mm. Anther color: Close to 82D. Pollen amount: Moderate. Pollen color: Close to 155B. Pistils: Quantity per flower:

One. Pistil length: About 4.7 mm. Stigma shape: Tapering. Stigma color: Close to NN155D. Style color: Close to NN155D. Ovary color: Close to 145C.

*Seeds/fruits*.—Seed and fruit production have not been observed.

Disease/pest resistance: Plants of the new *Angelonia* have not been noted to be resistant to pathogens and pests common to *Angelonia*.

Garden performance: Plants of the new *Angelonia* have been observed to have good garden performance and tolerate rain, wind and temperatures ranging from about 5° C. to about 40° C.

It is claimed:

1. A new and distinct *Angelonia* plant named 'Sungelobu' as illustrated and described.

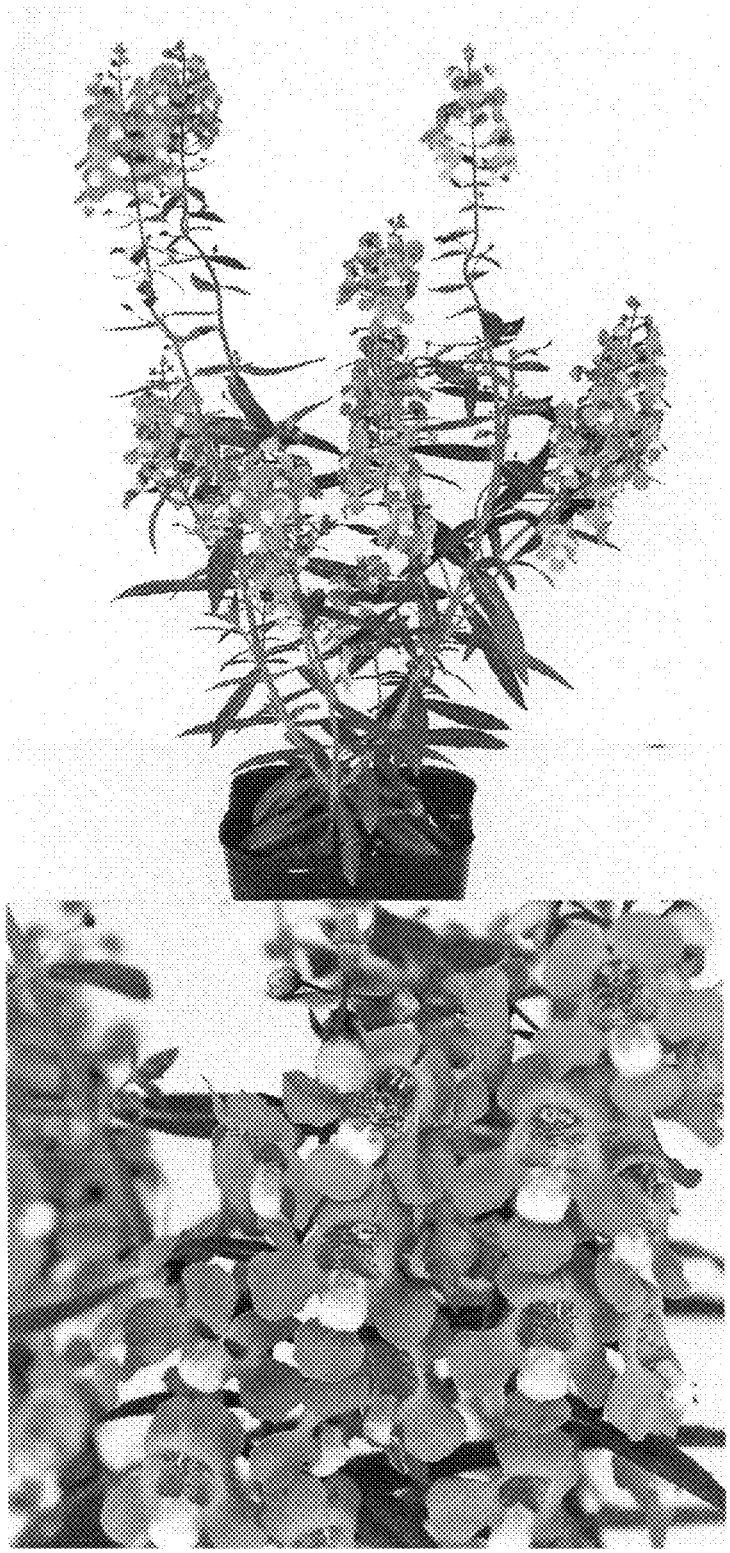

* * * * *